(12) United States Patent
Natarajan et al.

(10) Patent No.: US 9,116,150 B2
(45) Date of Patent: Aug. 25, 2015

(54) METHOD OF AND DEVICE FOR PACKING A CHROMATOGRAPHY COLUMN

(75) Inventors: Venkatesh Natarajan, Brighton, MA (US); Anthony Frederick Mann, Malmesbury (GB); Daniel Schubnel, Neuve-Eglise (FR)

(73) Assignee: EMD Millipore Corporation, Billerica, MA (US)

( * ) Notice: Subject to any disclaimer, the term of this patent is extended or adjusted under 35 U.S.C. 154(b) by 963 days.

(21) Appl. No.: 12/287,189

(22) Filed: Oct. 7, 2008

(65) Prior Publication Data

US 2010/0084342 A1      Apr. 8, 2010

Related U.S. Application Data

(60) Provisional application No. 61/003,631, filed on Nov. 19, 2007.

(51) Int. Cl.
*G01N 30/56*        (2006.01)

(52) U.S. Cl.
CPC .......... *G01N 30/56* (2013.01); *G01N 2030/565* (2013.01)

(58) Field of Classification Search
CPC .......................... G01N 30/56; G01N 2030/565
USPC ..................... 210/656, 635, 198.2; 141/12, 80
See application file for complete search history.

(56) References Cited

U.S. PATENT DOCUMENTS

| | | | |
|---|---|---|---|
| 3,587,669 A * | 6/1971 | Vabo | 141/12 |
| 3,856,681 A | 12/1974 | Huber | |
| 4,065,384 A | 12/1977 | Pandey et al. | |
| 4,175,037 A * | 11/1979 | Benney et al. | 141/12 |
| 4,276,061 A * | 6/1981 | Nestrick et al. | 95/88 |
| 4,469,601 A | 9/1984 | Beaver et al. | |
| 4,549,584 A * | 10/1985 | Morin et al. | 141/73 |
| 4,769,141 A * | 9/1988 | Couillard | 210/198.2 |
| 4,830,921 A * | 5/1989 | Kitayama et al. | 428/406 |
| 4,857,187 A * | 8/1989 | Ito | 210/198.2 |
| 5,051,176 A * | 9/1991 | Miyano et al. | 210/198.2 |
| 5,141,635 A * | 8/1992 | LePlang et al. | 210/198.2 |
| 5,167,809 A * | 12/1992 | Mann et al. | 210/198.2 |
| 5,200,471 A * | 4/1993 | Coleman et al. | 525/326.9 |
| 5,466,377 A * | 11/1995 | Grandics et al. | 210/635 |
| 5,833,861 A * | 11/1998 | Afeyan et al. | 210/656 |
| 6,444,122 B1* | 9/2002 | Van Davelaar | 210/198.2 |
| 6,740,241 B1* | 5/2004 | Dickson | 210/656 |
| 7,238,282 B2* | 7/2007 | Perreault et al. | 210/198.2 |
| 7,261,812 B1* | 8/2007 | Karp et al. | 210/198.2 |
| 7,674,383 B2* | 3/2010 | Rahn et al. | 210/656 |
| 2002/0166816 A1* | 11/2002 | Allen et al. | 210/656 |
| 2003/0146159 A1* | 8/2003 | Guiochon | 210/656 |
| 2004/0007530 A1* | 1/2004 | McNeff et al. | 210/656 |
| 2006/0113232 A1* | 6/2006 | Dunkley et al. | 210/198.2 |
| 2007/0181501 A1* | 8/2007 | Hoffmann et al. | 210/656 |

(Continued)

*Primary Examiner* — Ernest G Therkorn
(74) *Attorney, Agent, or Firm* — EMD Millipore Corporation

(57) ABSTRACT

A method and device for packing a chromatography column formed of one or more vibration devices attached to top and/or bottom flanges of the column. Media is added in one or more steps to the column, allowed to settle under the effects of gravity and then subjected to one or more treatments of vibration from the vibration devices until a suitably packed column is obtained. Liquid used to suspend the media while being placed into the column may be at least partially removed before or during the vibration step(s). The remaining liquid is then removed or replaced after the packing has been obtained.

13 Claims, 4 Drawing Sheets

(56) References Cited

U.S. PATENT DOCUMENTS

2007/0207500 A1* 9/2007 Bian et al. ............... 435/7.1
2007/0215548 A1* 9/2007 Zhou ........................ 210/656
2007/0219358 A1* 9/2007 Zhou ........................ 530/414
2010/0084342 A1* 4/2010 Natarajan et al. ......... 210/656

* cited by examiner

METHOD OF AND DEVICE FOR PACKING A CHROMATOGRAPHY COLUMN

CROSS-REFERENCED TO RELATED APPLICATIONS

This application claims the benefit of priority of U.S. Provisional Patent Application No. 61/003,631, filed on Nov. 19, 2007, the entire contents of which are incorporated by reference herein.

The present invention relates to a method and device for packing a chromatography column. More particularly, it relates to a method and device for packing a chromatography column using vibration.

BACKGROUND

Packing chromatography columns is as much an art as it is a science. Even the smallest of columns used in the analytical laboratory can be packed incorrectly leading to inconsistent results.

The most common problems in packing lead to channeling or gaps in the media bed through which the liquid and components to be chromatographed preferentially flow, leading to inconsistent results.

Numerous methods have been developed to attempt to obtain consistent packings. Many have used a dynamic flow of the media in a slurry formed of the media and a liquid to obtain a suitable packing.

Some have added the use of vibration during this dynamic packing to help the consistency of the packing effort. Others have used vibration in the slurry before it is added to the column to create as uniform a suspension of media in the slurry as possible.

While all of these efforts work to a large extent, they all require much effort and the use of large volumes of liquid to do so. What is needed is a simple method and device for packing columns regardless of size. The present invention provides such a method and device.

SUMMARY OF THE INVENTION

The present invention is a method and device for packing a chromatography column with a chromatographic media. The invention consists of a column having one or more vibrational device attached to its outer surface. A slurry of media and a liquid of choice (aqueous or non-aqueous depending upon the media selected) is put into the column in one or more portions and allowed to settle into a loose bed under the effect of gravity. The settled bed is then subjected to one or more sequences of vibration from the one or more vibration devices on the column to cause the bed to condense and form a uniformly packed bed. The column is then closed and the column is run as is typical in the art.

It is an object of the present invention to provide a method of packing a chromatography column comprising the steps of providing a chromatography column and a media for packing within the column, forming a slurry with the media and a liquid, adding at least a portion of the slurry to the column, allowing the at least a portion of the slurry to settle under gravity, vibrating the slurry in the column and removing the liquid from the column.

It is an object of the present invention to provide a method of packing a chromatography column comprising the steps of providing a chromatography column having one or more vibration devices attached to its outer surface and a media for packing within the column, forming a slurry with the media and a liquid, adding at least a portion of the slurry to the column, allowing the media to settle under gravity to form a loose bed, activating the one or more vibration devices to vibrating the slurry in the column and removing or replacing the liquid from the column to form a packed bed of media.

It is an object of the present invention to provide a method of packing a chromatography column comprising the steps of providing a chromatography column having one or more vibration devices attached to its outer surface and a media for packing within the column, forming a slurry with the media and a liquid, adding a first portion of the slurry to the column, allowing the media of the first portion to settle, activating the one or more vibration devices to vibrating the first portion of slurry in the column while removing the liquid from the column to form a packed bed of media, adding at least a second portion of the slurry, allowing at least the second portion of the media to settle under gravity, activating the one or more vibration devices to vibrating the second portion of slurry in the column and removing or replacing the liquid of the slurry from the column to form a packed bed of media.

It is an object of the present invention to add the slurry in two or more steps and the slurry is vibrated after each addition of slurry.

It is an object of the present invention to provide a hard media for the method selected from porous glass, porous silica and porous plastics.

It is an object of the present invention to provide two or more vibration devices evenly spaced from each other around a circumference of the column wall.

It is an object of the present invention to provide a device for packing a chromatography column comprising a column having a vertical wall, the vertical wall having an inner and outer surface, a lower plate having one or more ports, said lower plate being selected from the group consisting of fixed plates and adjustable plates, an adjustable upper plate and one or more vibration devices mounted to the column. Preferably, the one or more vibrator devices are located either on the flange of the lower plate or the top flange of the column wall.

It is an object of the present invention to provide two or more vibration devices are evenly spaced apart from each other around a circumference of the outer surface of the vertical wall.

IN THE DRAWINGS

DETAILED DESCRIPTION

The present invention relates to a method and device for packing a chromatography column.

Figure 1:
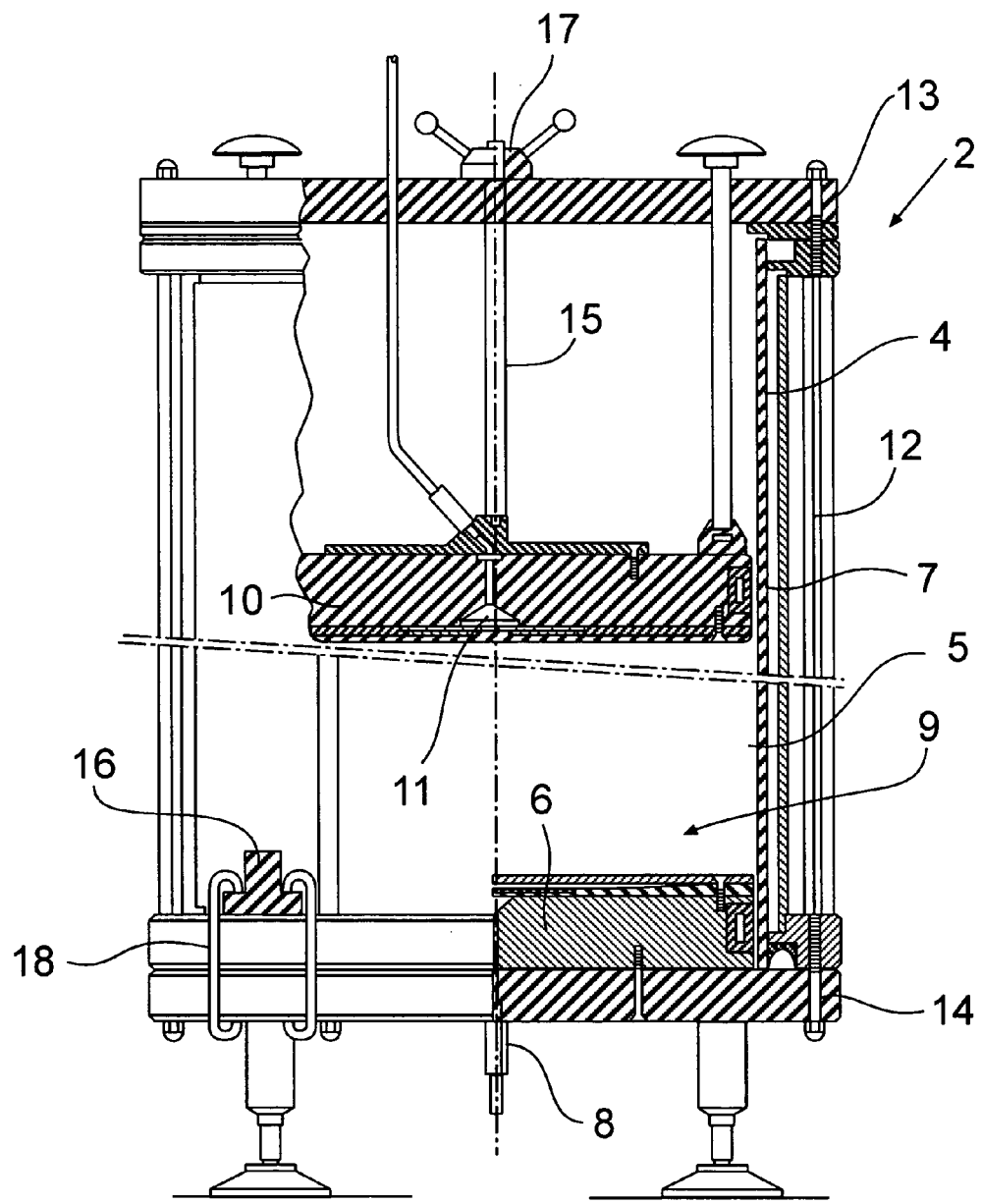
FIG. 1 shows a device according to the present invention in cross sectional view.

FIG. 1 shows one device that can be used in the present invention. It comprises a column 2 having a vertical wall 4 that forms the body of the column. The vertical wall 4 has an inner surface 5 and an outer surface 7. The area 9 within the inner surface 7 of the wall 4 provides the space 9 for the chromatography media and the lower plate 6 and upper plate 10.

The lower plate 6 is attached to the bottom of the vertical wall as is well known in the art. The lower plate 6 may be fixed or adjustable (movable) into or out of the column as is desired. A port 8 is formed in the lower plate 6 and is in selected fluid communication with the space 9 generally through a valve arrangement (not shown) that selectively opens and closes access to the space 9 as desired.

The upper plate 10 or adjuster plate as it is commonly called is attached above the wall 4 to the column 2 and is movable above and within the space 9 to provide a selectively closed environment for the media (not shown) in the space 9. One or more ports 11 are formed in the upper plate and are in selected fluid communication with the space 9 generally through a valve arrangement (not shown) that selectively opens and closes access to the space 9 as desired.

The use of threaded rods 12 are used to support and connect the upper flange 13 to the bottom flange 14 with column wall 4 in between in a liquid tight manner. Screw 15 mounted through the upper flange 13 and attached to the upper plate 10 allows the upper plate to move into and out of the space 9 as needed. While shown as being manually driven by turning device 17 it can be automatically driven and can use hydraulic lifts (not shown) if desired to pull the upper plate 10 out of and above the wall 4 to expose the space 9 for loading of media or repairs.

One or more vibration devices 16 are placed adjacent to the outer surface 7 of the wall 4. Preferably, they are temporarily attached to either the upper or lower flange 13, 14 or both so they may be removed during cleaning or chromatographic operations to avoid damage to the devices 16. If more than one device 16 is used, it is preferred that they be evenly spaced from each other about the circumference of the wall 4. As shown in FIG. 1, at least one device 16 is mounted to the lower flange 14 through the use of two or more clamps 18, such as C-clamps.

Vibration devices can be selected from a range of pneumatically driven roller or turbine vibrators. These vibrators are capable of generating vibrations with frequencies in the 6000-30000 Hz. The frequency of vibrations can be controlled by controlling the supply pressure. Such devices are available from OLI Vibrators, Inc and are commonly used in the powder processing Industries.

A method of using the device is as follows.

A column having one or more vibration devices arranged on the column, preferably on its top and/or bottom flange.

A chromatography media is formed into a slurry with a liquid which can be aqueous based such as water, saline solutions, various chromatography buffers, water alcohol blends and the like or non-aqueous based such as various alcohols depending on the media selected. The amount of liquid used should be sufficient to create a free flowing slurry. Typically the liquid will be from about 10 to about 90% of the volume of the slurry, preferably 30-70% and more preferably about 30 to about 50% of the volume of the slurry.

The slurry is added to the column either through the open top of the column into the space 9 as the upper plate 10 has been moved out of the column or through the one or more ports 11 formed in the upper plate 10 or through an ISOPAK® valve (Millipore Corporation of Billerica, Mass.). The media is allowed to settle out of the slurry.

After settling under the effect of gravity, the media is in the form of a loose bed. One or more sequences of vibration are applied to the bed through the one or more vibration devices 16 arranged on the column bottom or top flange. This is preferably followed by flow of liquid through the column to create a compact uniform bed.

In another embodiment of the present invention, settling can be conducted with periodic intervals of vibration such that a period of vibration is followed by a period of settling without vibration until the bed of desired packing consistency is obtained.

In a further embodiment, the use of the flow of fluid through the media as it settles can in some instances help with the settling and packing. This maybe a steady flow or intermittent or pulsed flow cycles of one or more times. Intermittent flows can be from about 30 seconds to about 5 minutes each and when used more than once in a single packing step can be spaced apart as needed, preferably from about 1 minute to about 10 minutes between each flow pulse.

In a different embodiment the combination of flow packing and vibration during the bed formation can be used.

The amount of time for vibration and when it is used will vary depending upon the media selected, the liquid used in the slurry, the depth of the bed desired and the desired level of packing to be obtained and can be easily determined with simple experimentation by one of ordinary skill in the art. Typically, the use of one or more vibration sequences of from about 1 to about 10 minutes, preferably from about 1 to about 5 minutes can be used.

In those embodiments in which vibration occurs at least during settling, it is preferred that the vibration be for about 30 seconds to about 3 minutes followed by no vibration for a period of from about 1 minute to about 5 minutes, preferably the sequence is for about 1 minute of vibration followed by about 2 minutes of no vibration. This can be repeated if necessary or desired as many times as needed to obtain the desired packed bed.

In either embodiment, the upper plate 10 is then moved against the upper surface of the bed and the chromatography bed is now ready for equilibration and/or use.

This invention works with all types of chromatography media including softer or compressible media such as agarose based media such as Sepharose® media or MabSelect® media available from GE Healthcare or hard media such as porous silica, porous plastic such as POROS® media from Perseptive Biosystems Inc, or porous glass, preferably controlled pore glass such as CPG® media from Millipore Corporation, more particularly controlled pore glass that has a ligand attached to it, such as ProSep® A media from Millipore Corporation.

EXAMPLES

Example #1

A QuikScale® column (Millipore Corporation of Billerica, Mass.) of 450 mm diameter was obtained. A known quantity of CPG® controlled pore glass chromatography resin of 100 µm diameter and a pore size of 1000 A (Millipore Corporation of Billerica, Mass.) was transferred to the column in a slurry formed of the resin and reverse osmosis (RO) water. This quantity of resin was packed in four different ways:

1) Gravity—Allow the packed bed to form by settling under gravity alone
2) Flow pack—Allow the packed bed to form by application of flow
3) Stop Flow—Form the packed bed by flow pack and then subject it to 4-5 cycles of periodic flow (flow on for 2 minutes and off for 3 minutes)
4) Vibration—Allow the packed bed to form by allowing to settle under gravity with periodic input of vibrational energy (on for 1 minute and off for 2 minutes). The vibrational energy was input to the column by clamping a single OR65 vibrational device (OLI Vibrators, Inc, Norcross, Ga., USA) on the bottom flange of the column.

Figure 2:
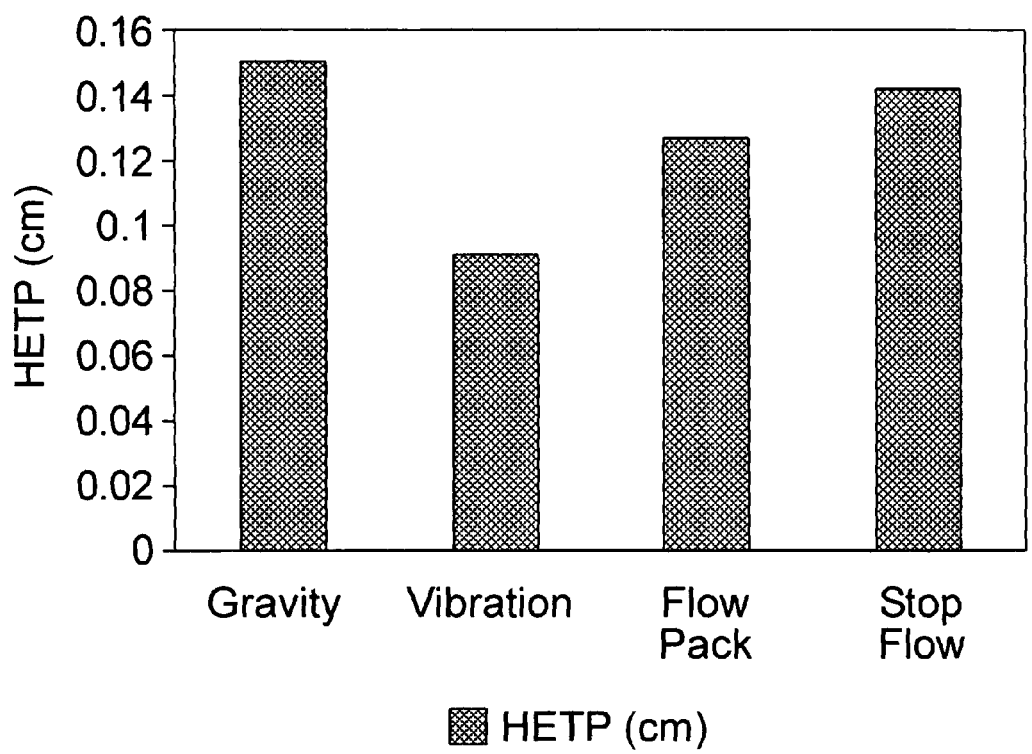
FIG. 2 shows a bar graph with the HETP results of Example 1.

The resin was unpacked and re-slurried prior to each packing method. Each packed bed was qualified using an injection of a 0.5M Sodium chloride solution in RO water. The Height Equivalent to a Theoretical Plate (HETP) of the sodium chloride peak exiting the packed bed was used as the comparison metric. The lower the HETP, the more efficient was the resultant bed. The HETP obtained with each packed bed is illustrated in FIG. 2. As is evident from the figure, the vibration packing technique yielded the most efficient bed.

Example #2

An IPP 1600×600×500 column rated to 3 bar (Millipore Corporation of Billerica, Mass.) of 1.6 meters (hydraulically operated and fitted with IsoPak® valves in both plates) was obtained.

A known quantity of CPG® controlled pore glass chromatography resin of 100 micron diameter and a pore size of 1000 angstroms (Millipore Corporation of Billerica, Mass.) was transferred to the column in a slurry formed of the resin and reverse osmosis (RO) water. The media was packed the following ways:

1) Stop flow with fluidization—Following transfer of media into the column, the media was allowed to settle under gravity, subsequently it was fluidized at 100 cm/hr for 2 column volumes and finally flow was applied to form a settled bed. Following the formation of the settled bed, the latter was subjected to 4-5 cycles of periodic flow (flow on for 2 minutes and off for 3 minutes)
2) Stop flow with vibration—Following transfer of media into the column, flow was immediately applied to the column to form settled bed. Following the formation of the settled bed, the latter was subjected to periodic vibration followed by flow (1 min vibration+1 minute flow). The vibrational energy was input to the column by clamping a single OR100 vibrational device (OLI Vibrators, Inc, Norcross, Ga., USA) on the bottom flange of the column.
3) Vibration (1 vibrator)—Following transfer of media into the column, the media was allowed to settle under gravity with periodic input of vibrational energy (1 minute on, 2 minutes off) till the formation of a stable packed bed. The vibrational energy was input to the column by clamping a single OR100 vibrational device (OLI Vibrators, Inc, Norcross, Ga., USA) on the bottom flange of the column.
4) Vibration (3 Vibrators)—Following transfer of media into the column, the media was allowed to settle under gravity with periodic input of vibrational energy (1 minute on, 2 minutes off) till the formation of a stable packed bed. The vibrational energy was input to the column by clamping three OR100 vibrational device (OLI Vibrators, Inc, Norcross, Ga., USA) on the bottom flange of the column and evenly spaced from each other.

Each packed bed was qualified using an injection of a 0.5M Sodium chloride solution in RO water. The Height Equivalent to a Theoretical Plate (HETP) of the sodium chloride peak exiting the packed bed was used as the comparison metric. The lower the HETP, the more efficient the resultant bed.

Figure 3:
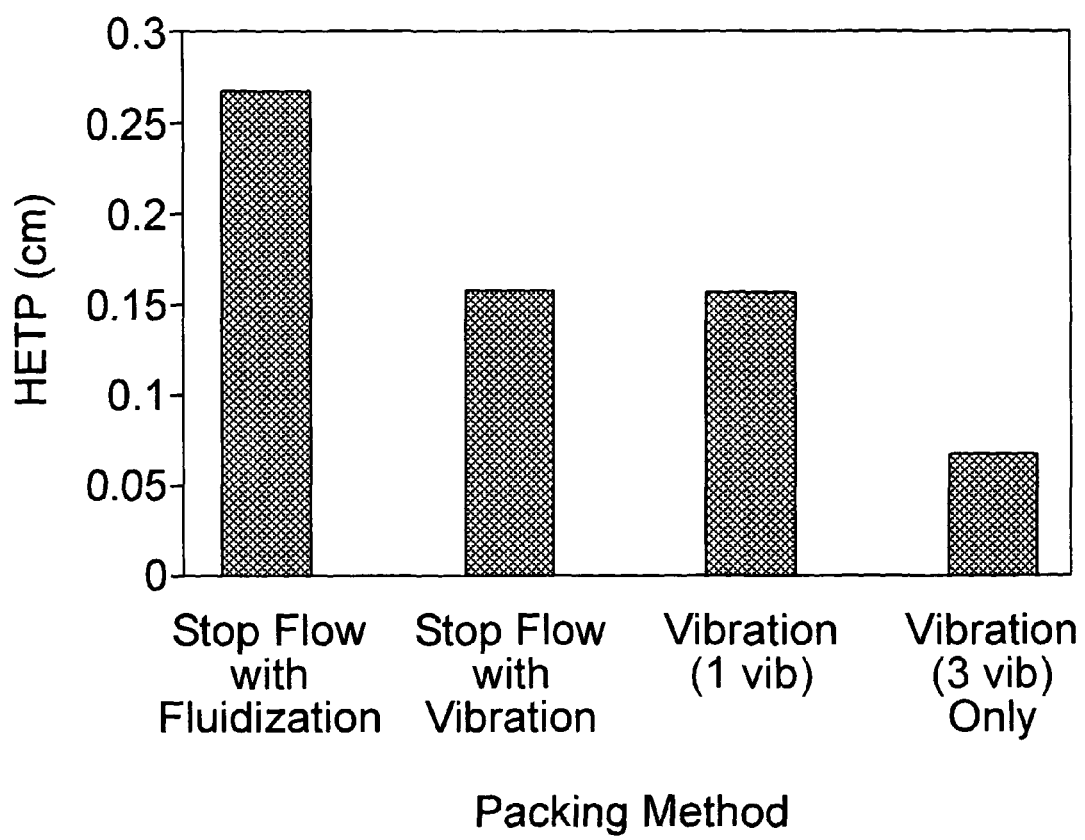
FIG. 3 shows a bar graph with the HETP results of Example 2.

The HETP obtained with each packed bed is illustrated in FIG. 3. As is evident from the figure, inclusion of vibration in the packing technique improves the performance of the bed. The use of vibration alone, when the vibrational energy is input with three evenly spaced vibrating devices yields the most efficient bed.

Figure 4:
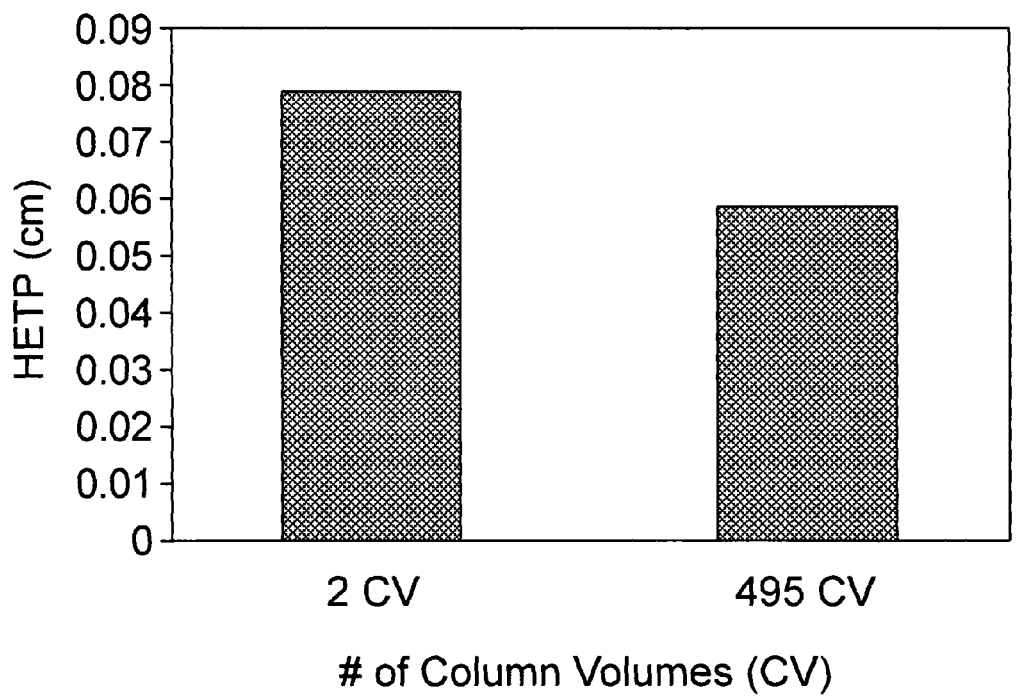
FIG. 4 shows a bar graph with the results of Example 2 over time.

The packed bed obtained by vibrating with three vibrational devices was subjected to continuous flow for close to 500 column volumes (CV) to test for its stability. FIG. 4 illustrates the HETP of qualification sodium chloride (0.5M in RO water) pulses at the beginning and end of the stability test. As is evidenced by the lower HETP at the end of the test, the packed bed was stable to continuous operation.

Thus, Examples 1 and 2 demonstrate that the use of vibration, in conjunction with flow or without flow, yields more efficient and stable packed beds than with flow alone.

What is claimed:

1. A method of packing a chromatography column comprising the steps of: providing a chromatography column having two or more vibration devices attached to its outer surface, and providing a controlled pore glass media with a Protein A ligand and a liquid buffer solution; forming a slurry with the media and the buffer solution, wherein the buffer solution is present from about 10 to about 90% of the volume of the slurry, adding the slurry to the column, allowing the slurry to settle under gravity, activating the vibration devices to generate vibrations with frequencies in the 6000-30000 Hz one or more times to vibrate the slurry in the column at periodic intervals, wherein the vibration devices vibrate from about 30 seconds to about 3 minutes followed by no vibration for a period of about 1 minute to about 5 minutes, and removing the liquid of the slurry during the periodic vibration steps to form a packed bed of media, wherein the packed bed has a lower Height Equivalent to a Theoretical Plate (HETP) compared to a column having only one vibration device.

2. The method of claim 1 wherein the controlled pore glass media has a 100 μm diameter and pore size of 1000 A.

3. The method of claim 1, wherein the column comprises three or more vibration devices on the outer surface of the column.

4. The method of claim 3, wherein the three or more vibration devices are evenly spaced apart on the outer surface of column.

5. The method of claim 3, wherein the vibration devices vibrate for about 1 minute followed by no vibration for about 2 minutes.

6. The method of claim 3, wherein the vibration devices are clamped onto the outer surface of the column.

7. The method of claim 3, wherein the column comprises a bottom flange and the vibration devices are evenly spaced on the bottom flange of the column.

8. The method of claim 1, wherein the two or more vibration devices are evenly spaced apart on the outer surface of the column.

9. The method of claim 1, wherein the vibration devices vibrate for about 1 minute followed by no vibration for about 2 minutes.

10. The method of claim 1, wherein the vibration devices are clamped onto the outer surface of column.

11. The method of claim 1, wherein the column comprises a bottom flange and the vibration devices are evenly spaced on bottom flange of the column.

12. The method of claim 1, wherein the liquid is an aqueous liquid.

13. The method of claim 2, wherein the liquid is an aqueous liquid selected from the group consisting of water, saline solutions, buffer solutions and water/alcohols blends.

* * * * *

UNITED STATES PATENT AND TRADEMARK OFFICE
CERTIFICATE OF CORRECTION

PATENT NO.       : 9,116,150 B2  
APPLICATION NO.  : 12/287189  
DATED            : August 25, 2015  
INVENTOR(S)      : Venkatesh Natarajan et al.

Page 1 of 1

It is certified that error appears in the above-identified patent and that said Letters Patent is hereby corrected as shown below:

Claims

In column 6, line 62, in claim 13 delete "claim 2" and insert -- claim 12 --, therefor.

Signed and Sealed this  
Fifth Day of January, 2016

Michelle K. Lee  
*Director of the United States Patent and Trademark Office*